(12) United States Patent
Fujii

(10) Patent No.: US 7,334,300 B2
(45) Date of Patent: Feb. 26, 2008

(54) CLIP USED FOR CLIPPING A HOLLOW MEMBER

(75) Inventor: Sumiya Fujii, Hiroshima (JP)

(73) Assignee: JMS Co., Ltd., Hiroshima-shi (JP)

( * ) Notice: Subject to any disclaimer, the term of this patent is extended or adjusted under 35 U.S.C. 154(b) by 98 days.

(21) Appl. No.: 10/490,856

(22) PCT Filed: Sep. 27, 2002

(86) PCT No.: PCT/JP02/10005

§ 371 (c)(1),
(2), (4) Date: Aug. 18, 2004

(87) PCT Pub. No.: WO03/029092

PCT Pub. Date: Apr. 10, 2003

(65) Prior Publication Data

US 2004/0255436 A1    Dec. 23, 2004

(30) Foreign Application Priority Data

Sep. 28, 2001    (JP) ............................. 2001-299686

(51) Int. Cl.
*F16B 2/10* (2006.01)
(52) U.S. Cl. .................... 24/30.5 R; 24/518
(58) Field of Classification Search ............ 24/30.5 R, 24/30.5 P, 518, 543; 251/9, 10; 383/68, 383/78, 81; 606/157, 158, 120; 604/335
See application file for complete search history.

(56) References Cited

U.S. PATENT DOCUMENTS

| 3,363,293 | A | * | 1/1968 | Nemrod et al. ........... 24/30.5 P |
| 4,551,888 | A |   | 11/1985 | Beecher |
| 4,887,335 | A |   | 12/1989 | Folkmar |
| 5,125,133 | A |   | 6/1992 | Morrison |
| 5,608,382 | A | * | 3/1997 | Webb et al. ............. 340/573.4 |
| 5,713,108 | A | * | 2/1998 | Solomon et al. ......... 24/30.5 R |
| 6,058,572 | A | * | 5/2000 | Folkmar .................. 24/30.5 R |

FOREIGN PATENT DOCUMENTS

| GB | 2 188 085 A | 9/1987 |
| JP | 1-240452 A | 9/1989 |
| JP | 1-254558 A | 10/1989 |
| JP | 119123/1988 | 3/1990 |
| WO | WO 92/03353 A | 3/1992 |
| WO | WO 9203353 A1 * | 3/1992 |

\* cited by examiner

*Primary Examiner*—James R. Brittain
(74) *Attorney, Agent, or Firm*—Westerman, Hattori, Daniels & Adrian, LLP.

(57) ABSTRACT

A clip that is able to form a separate space in the hollow member such as flexible tube or bag-like article and the like or to block its opening part by clipping hollow member. The clip includes two plate-like members with one plate-like member having a groove formed in a longitudinal direction of the plate-like member and the other plate-like member having a projection part formed in the longitudinal direction. The form of the projection part is made highest in a vicinity of a central part of the clip and lowest at both end parts of the plate-like member.

5 Claims, 2 Drawing Sheets

CLIP USED FOR CLIPPING A HOLLOW MEMBER

TECHNICAL FIELD

The present invention relates to a clip that blocks a flexible hollow member such as tube or bag-like article and the like, to divide said flexible hollow member such as tube or bag-like article and the like in a separate space.

As for said bag-like article, bag for medical or pharmaceutical use such as infusion solution bag and the like can be exemplified, but it is not limited for medical use, and it can be used in fields where it is necessary to form an independent space by blocking flexible hollow member with a clip.

Furthermore, the clamp of the present invention is especially useful as a clip to be used to form a separate space by blocking tube or flexible hollow member and the like, as described above. However, it can be obviously used as a clip to block the opening part of tube or flexible hollow member and the like.

BACKGROUND ART

There is a clip that is used for subdividing solution chambers in bags for medical or pharmaceutical use that are used as infusion solution bags or dialysate bags and the like, disclosed in Utility Model Publication No. 5-8998. This clip has a construction wherein catching parts fixing each other are provided to each of both end parts of two clip pieces formed separately, and a linear holding part that clips both sides of the infusion solution bag in the central longitudinal direction excluding the prescribed area at both ends of each clip piece, is formed.

Moreover, there is a clamp that clips tube or bag to seal the inner space of the clipped object in a liquid tight condition, disclosed in Japanese Patent Publication No. 4-193179. It is composed of the following: a catching means located at an end of the clamp, binding two plate-like members in a detachable way; a clipping part composed of two plate-like members having pressing projecting parts being parallel to each other, in the longitudinal direction of its inner surface; a detachable latching means maintaining said clipping part in a condition that the clipped object is clipped; and a grasping part located at the other end of the clamp, to give a force to said clipping part for clipping said clipped object by grasping with the finger and the like.

There is a clamp that clips tube or bag to seal the inner space of the clipped object in a liquid tight condition, disclosed in Japanese Laid-Open Patent Application No. 2000-229648. This is a clip that clips the prescribed part of the clipped object from both sides, binding a pair of pinching levers by the axe in a detachable and oscillating way at one end of the clip. The other end part of both pinching levers is composed so that it is able to fix and latch by a latching means. An insertion channel is formed along the longitudinal direction of the pinching lever in the facing surface from the second pinching lever to the first pinching lever. An insertion line section, which is abutting to the side wall part by being inserted to this insertion channel, is projectingly formed to the facing surface from the first pinching lever to the second pinching lever. It has a construction that a film material to be clipped is pressure-bonded between the insertion channel of the second pinching lever and the insertion line section of the first pinching lever inserted into the insertion channel.

As for the clamp sealing the opening of the bag and the like, there is one disclosed in Japanese Patent Publication No. 2-60580. As for the clip comprising a clipping means wherein two rims are facing each other by the hinge binding, and a locking element provided at a free end of the rim, the rim comprises a leg being able to press resiliently to the side facing to the rim; and rim 2 provides a channel having a wide opening that can accept said leg together with the object to be clipped, and a taper inner wall surface that leads leg 3 to the narrow back part.

As described above, as for clips used to block member the opening part of a hollow member such as flexible tube or bag-like article and the like or to form a separate space, by sealing said hollow member, various clips having a pair of plate-like members, provided with a projection of a constant form in the longitudinal direction of one of the plate-like members, and a groove in the longitudinal direction of the other plate-like member, having a structure ensuring the airtight condition of the sealed part by the engagement of said projection and groove, have been proposed. However, as for a clip having above-mentioned structure, there were the following problems such as: (1) it is difficult to maintain the airtight condition of the central part, as the central part of the plate-like member opens widely compared to the end part, due to the repulsive force of the hollow member. (2) due to the excess projection at both ends of the clamp and to the groove depth, it happens that a distinct deformation due to sealing occurs to the flexible tube or hollow member having been clipped, and as the distinct deformation due to sealing occurs, even by releasing the clamp and pressing said flexible tube or hollow member to communicate the fluid, due to the distinct deformation due to sealing, the communication of the fluid was inhibited and a significant pressing force was necessary to communicate.

Particularly, there is a stronger tendency of the mark mentioned above to occur due to extreme conditions such as storage for a long term and process of sterilization or the like, thus it was difficult to ensure the communication of the fluid, without decreasing or lowering the airtight function of the clip. Furthermore, as for the above-mentioned problem (1), that it is difficult to ensure the airtight condition in the central part in the longitudinal direction of the clip, it can be solved on some level by making the projection at both ends of the clamp higher, and making the depth of the groove deeper. However, by adapting such construction, there was a problem that the deformation due to sealing as mentioned above would be more distinct.

The present invention is to provide a clip that is able to form a separate space in a hollow member such as flexible tube or bag-like article and the like or to block its opening part, by clipping said hollow member, and that has solved the above-mentioned problems.

SUMMARY OF THE INVENTION

The present invention provides a clip that is able to form a separate space in a hollow member such as flexible tube or bag-like article and the like or to block its opening part, by clipping said hollow member between one of the plate-like members having a groove formed in the longitudinal direction and the other plate-like member having formed a projection of a constant form in the longitudinal direction, wherein the height of the projection of said plate-like member is made to be highest in the central part of the plate-like member, and lowest at both ends of the plate-like member, and thus solved the above-mentioned problem (1) and provides a clamp which the circulation was improved without lowering the airtight function.

In other words, the present inventor noted that: as for the clip having a structure ensuring the airtight condition by the engagement of the groove formed in said plate-like member and the projection of a constant form, in case the airtight condition of a hollow member such as flexible tube or bag-like article and the like is ensured by clipping said hollow member with said groove and projection part, between one of the plate-like members having forming a groove in the longitudinal direction and the other plate-like member having formed a projection in the longitudinal direction, the cause that it is difficult to ensure the airtight condition in the central part of the plate-like member is that the space between the plate-like members in the vicinity of the central part of the plate-like member, clips the hollow member in a more widely opened and deformed manner compared to the space between the plate-like members at its end part. Therefore, in order to seal the hollow member in a liquid tight condition even in the vicinity of the central part of the plate-like member even such deformation of the plate-like member occurs, the present inventor made the projection form so that the height of the projection of the plate-like member according to the deformed condition of the plate-like member occurring when the plate-like member clips the hollow member, to be highest in the central part of the plate-like member, and lowest at the end part, and thus solved the above-mentioned problem (1).

As described above, as for the projection form of the plate-like member that composes the clip of the present invention, it is composed so that its height is set to be highest in the vicinity of the central part of the plate-like member, and lowest at the end part. However, as for said "vicinity part of the central part", it is not only related to the central part in the truest sense, but also to the area including the surrounding that is able to solve the above-mentioned problem (1).

As for the form of said projection, there is: a form becoming gradually high from the end part of the plate-like member toward the vicinity of the central part, according to the deformed condition of the plate-like member (former form); and a form becoming stepwise high from the end part toward the vicinity of the central part (latter form). However, as for the deformation of the plate-like member that actually takes place, it is gradually sloping toward the vicinity of the central part, and making an arc shape, the former form is preferable. Moreover, as for the height of said projection form, it is determined appropriately according to the deformed condition of the plate-like member determined by the material, form, its length and the like of the plate-like member, or by the material, the thickness of the membrane and the like of the hollow member being the clipped object, so that the hollow member can be sealed by ensuring sufficiently the liquid tight condition, even in the vicinity of the central part of the plate-like member.

As for the clip of the present invention, as the projection of the plate-like member constituting the clip has a form and height as mentioned above, it is possible to seal the hollow member being the clipped object with only the projection and the groove provided in the plate-like member, in a liquid tight condition. Furthermore, by adapting the form and the height of the projection form such as described above, it is possible to seal the hollow member in a liquid tight condition sufficiently, even when miniaturizing the form of the clamp of the present invention, including said plate-like member, or decreasing the rigidity of the plate-like member. Moreover, as it is described above, it is possible to decrease the rigidity of the plate-like member to seal in a liquid tight condition, there is an advantage that the range of selection of materials composing said plate-like members can be broader.

Furthermore, conventionally, as for the clip that seals the clipped object by clipping flexible hollow member between one of the plate-like members having a groove formed in longitudinal direction and the plate-like member having formed a projection of a constant form in longitudinal direction, it was not possible to seal the clipped object sufficiently in a liquid tight condition with only the projection and the groove provided in said plate-like member. Therefore, a high projection part was provided in the longitudinal direction at both sides of the projection part of the plate-like member, and the liquid tight condition was increased with the engagement with the other plate-like member having been provided with this high projection part and groove. However by making use of this engagement, there is a problem that the fluid circulation will be difficult after sealing, which is the above-mentioned problem (2). On the contrary, as for the clip of the present invention, it is possible to seal the clipped object sufficiently in a liquid tight condition with only the projection and the groove of the plate-like member of the clip as it is described above, it is not necessary to provide a high projection part that was necessary for the conventional clip as described above or to be a structure to be engaged with the other plate-like member having said high projection part and a groove, it is also possible to contribute to solve the above-mentioned problem (2).

As for the groove formed in the plate-like member of the clip of the present invention, two tooth-like structures being parallel can be exemplified. Especially, it is preferable that a tooth-like structure is a structure as shown in FIG. 2, and that a thin-walled part (7) is provided to the tooth part. By providing a thin-walled part (7) to the tooth parts (9,9) of the tooth-like structure, especially by providing it to the root part of the tooth part, the flexibility of the groove in the opening direction of the plate-like member will increase, and it will be possible to crimp the hollow member uniformly all the way long the longitudinal direction of the plate-like member. Therefore, as for the plate member providing a thin-walled part to the tooth part of the tooth-like structure, it is preferable that the height and the form of the projection form of the other plate-like member is highest in the vicinity of the central part of the plate-like member and lowest at the end part, as described above, but even the projection part does not have such structure, and that the form is such the height of the said projection part is the same through the longitudinal direction as it is for the clip conventionally used, the liquid tight condition when the hollow member is sealed, can be ensured sufficiently. Moreover, even it is a clip that uses a plate-like member having formed a projection part having the same height in the longitudinal direction, by forming a dimple in the plate-like member to facilitate the communication of the fluid of the plate-like member mentioned below, it is possible to improve the communication of the fluid, at the time the sealing condition of the clip is released.

Furthermore, as for the plate-like member of the clip of the present invention, it is preferable to form a dimple to facilitate the communication of the fluid on the clipping surface side. By forming such dimple, in case of performing fluid opening by releasing the clipping of the hollow member by the clip of the present invention, and even in case a distinct deformation due to sealing is made to the hollow member by said clipping, it will be formed in a shape that the relative sealing part is swollen into the dimple of said plate-like member. Therefore, when performing the communication of the fluid, said part with a swollen form becomes the flow fluid path to facilitate the communication of the fluid, and the fluid opening will be facilitated.

As for the dimple formed on said clipping surface side to facilitate the communication of the fluid, it is preferable that it is formed on the side end part of an optional position in the longitudinal direction of the plate-like member. Especially, it is more preferable that it is provided on the side end part in the vicinity of the central part of the plate-like member to perform the communication of the fluid most efficiently. Moreover, it is particularly preferable to provide it on both side ends facing each other in the vicinity of the central part of the plate-like member. Moreover, as for the technical means adapted to provide a dimple on the plate-like member to facilitate said communication of the fluid, it would be possible to improve significantly the communication of the fluid, even by adapting it to the conventionally known clip, not having a groove structure formed by a tooth-like structure having said projection form or having a thin-walled part. However, as for the clip of the present invention, a clip having all of each characteristics of the present invention described above, in other words, a clip wherein the projection form of said plate-like member is made to be highest in the vicinity of the central part of the plate-like member, and lowest at both end parts of the plate-like member; the groove of said plate-like member is formed with two tooth-like structures having a thin-walled part in the tooth part of the tooth-like structure; and having formed a dimple facilitating the communication of the fluid on at least one clipping surface of the plate-like member, is most preferable to attain the object.

As for each means mentioned above that the clip of the present invention has adapted to solve its technical object, it can be adapted by all the clips as long as it is a clip that is able to form a separate space in a hollow member such as flexible tube or bag-like article and the like or to block its opening part, by clipping said hollow member between one of the plate-like members having formed a groove in the longitudinal direction and the other plate-like member having formed a projection in the longitudinal direction. As for this type of clips, there are clips that has integrally the latching means and the part to be pressed, or clips that has the latching means in a place different from the part to be pressed, but it can be adapted any of the two types.

DETAILED DESCRIPTION OF THE INVENTION

Figure 1:
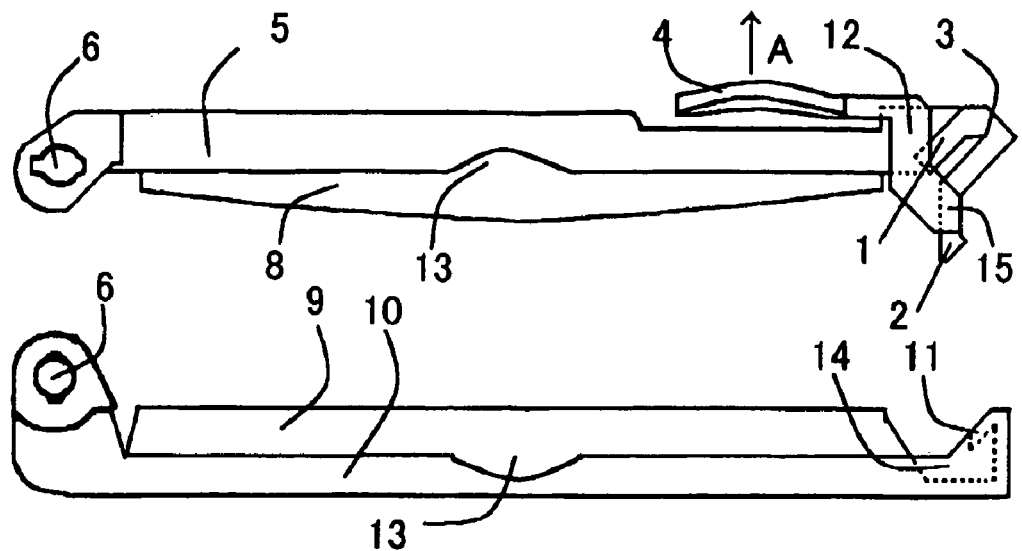
FIG. 1 illustrates the clip having plate members according to one embodiment of the present invention.
Figure 2:
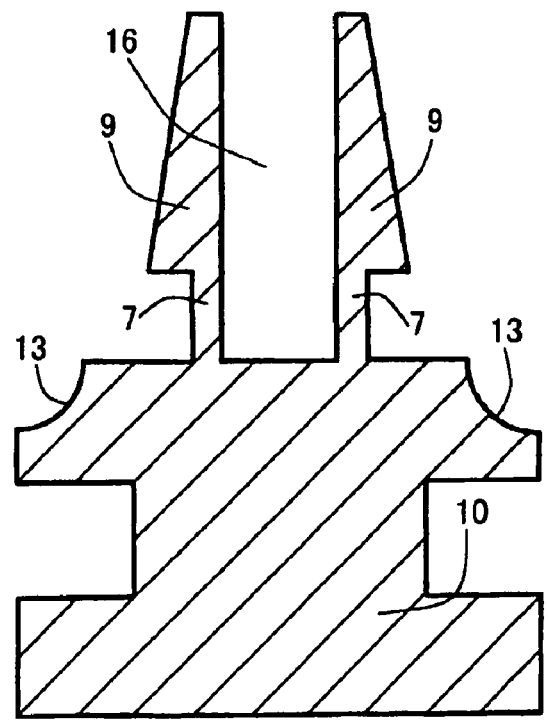
FIG. 2 is a cross sectional view of the plate member according to one embodiment of the present invention.
Figure 3:
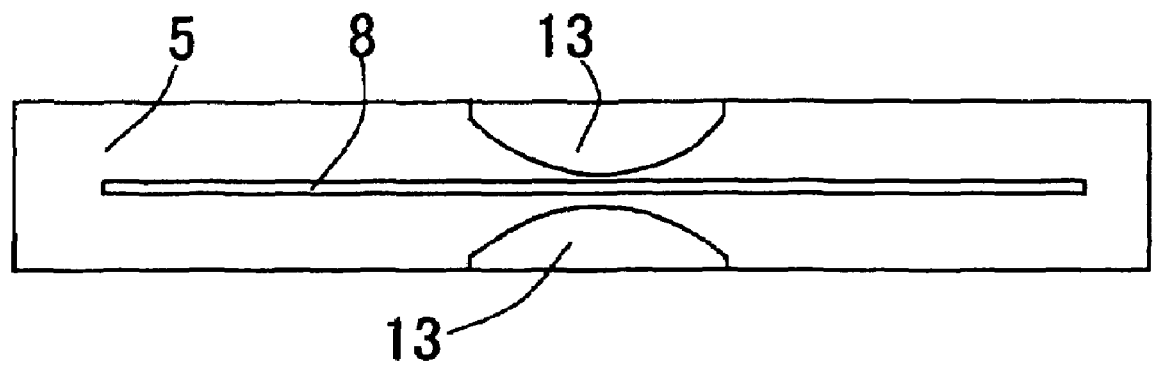
FIG. 3 illustrates a dimensional diagram of the plate member according to an embodiment of the present invention.
Figure 4:
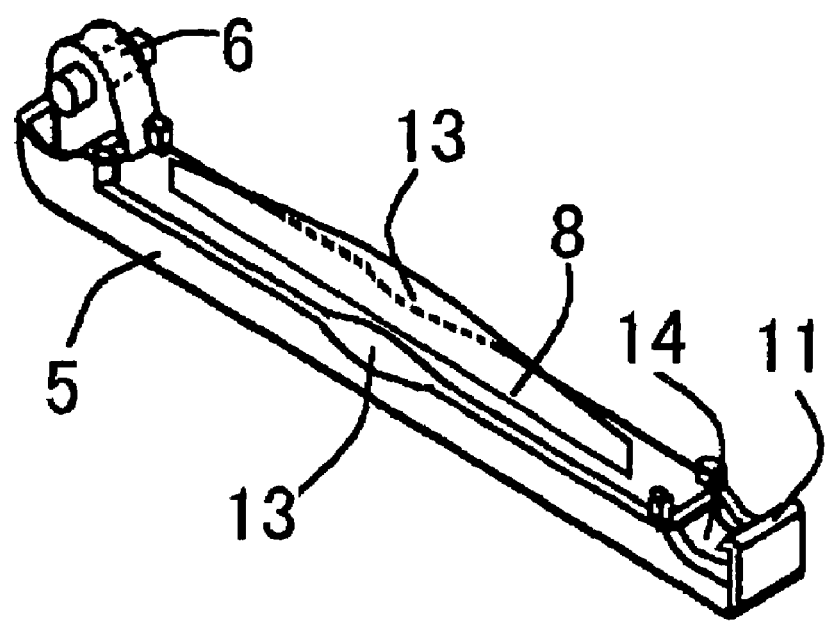
FIG. 4 is a perspective view of the plate member according to an embodiment of the present invention.

FIG. 1 is a figure that explains one example of a pair of the plate-like members composing the clip. FIG. 2 is a cross sectional view of the plate-like member at the dimple part, formed in the vicinity of the central part in longitudinal direction of the plate-like member composing the clip. FIG. 3 is a dimensional diagram of the plate-like member having the projection part, provided with a dimple on the vicinity of the central part in longitudinal direction of the plate-like member composing the clip (the latching part and the binding part of the plate-like member are omissioned). FIG. 4 is a perspective view explaining one example of the plate-like member composing the clip. In each of the figures mentioned above, 1 is the elastic member part of the latching member, 2 is the latching part (convex part) of the latching member, 3 is the supporting point of the latching member, 4 is the pull-tab, 5 is one of the plate-like members, 6 is the binding part of the plate-like member, 7 is the thin-walled part of the teeth of geta, 8 is the projection member formed along the longitudinal direction of the plate-like member possible to be inserted in a groove 16, formed in the longitudinal direction of the plate-like member, 9 is the teeth part of the tooth-like structure formed in the longitudinal direction of the plate member, 10 is the other plate-like member, 11 is the projection part composing the latching part, 12 is the band shape elastic member of the latching releasing member, 13 is the dimple, 14 is the through hole, 15 is the binding part of the elastic member part 1 and the band shape elastic member 12, 16 is the groove formed in the longitudinal direction of the plate-like member with two tooth-like structures.

The best embodiment of the present invention is explained in the following, in reference with the figures.

Plate-Like Member

As it is shown in FIG. 1, in one of the plate-like members (5) of the clip, a projection part (8) being highest in the vicinity of the central part of said plate-like member (5), and lowest in both end parts is formed. Moreover, a dimple (13) to facilitate said communication of the fluid is formed at both side parts facing each other in the vicinity of the central part of the plate-like member. Furthermore, at one end of said plate-like member, a catching means to catch both members and a latching means to latch both members are provided. At one of the plate-like members (10), as it is shown in FIGS. 1 and 2, a groove (16) in which said projection part (8) is to be inserted, are formed in the longitudinal direction of said plate-like member (10), having two tooth parts (9,9) of the tooth-like structures in which the root of the tooth parts of said tooth-like structures is a thin-walled structure (7), and furthermore, at the both side parts facing each other in the vicinity of the central part of the plate-like member, a dimple (13) to facilitate the opening is formed.

Moreover, it can be a clip structure having the tooth-like structure for the plate member (5), and having a projection part (8) at the plate-like member (10).

As for the clip of the present embodiment, a dimple (13) to facilitate the fluid opening is formed at both side end parts of in the vicinity of the central part of both plate-like members (5, 10). The dimple (13) can be formed in only one of the pair of the plate-like members, the position to form the dimple can be an optional position in the longitudinal direction of the plate-like member, or it can be formed in only one side. The most preferable embodiment is that the dimple (13) that facilitates the opening is formed on both side parts in the vicinity of the central part in the longitudinal direction of both plate-like members (5, 10), and it is preferable that said dimples are formed on both plate-like members, and are formed in a position so that they correspond each other between the upper and bottom part.

As for the clip of the present embodiment, a cutout parts (7,7) is formed in the outer surface of the root part of two tooth parts (9, 9) of the tooth-like structure, and the root part of the tooth of the tooth-like structures is formed to be a thin-walled structure, and can be a thin-walled structure by forming a cutout part in the inner surface. However, from the point of view of the simplicity of manufacturing, and that it is able to increase the flexibility of the groove, formed on the plate-like member, in the opening direction of the plate-like member, and to crimp the hollow member uniformly along the longitudinal direction of the plate-like member, the clip of the present embodiment is most preferable.

For the balance between the characteristics of the hinge required by the clip of the present invention, and the rigidity required to ensure the airtight condition of the tube or flexible hollow member, it is preferable to be made with polyoxymethylene resin (hereinafter referred as POM), polypropylene resin (hereinafter referred as PP resin), polycarbonate resin (hereinafter referred as PC resin), or to be made by mixing reinforcer such as glass fiber (hereinafter referred as GF), carbon fiber (hereinafter referred as CF) and the like to said resin. Especially, as the clip of the present embodiment has made the projection form of the plate-like member composing said clip to be high in the vicinity of the central part of the plate-like member, and to be low at both end parts of the plate-like member, and furthermore, formed a thin-walled structure to the tooth having a structure like teeth of geta, composing the groove of the plate-like member as described above, even by miniaturizing it, or by using plate-like member wherein the rigidity is lowered, it is possible to seal the hollow member sufficiently in a liquid tight condition. Therefore, it became possible to use polypropylene resin (hereinafter referred as PP resin) instead of polyoxymethylene resin (hereinafter referred as POM), that was mainly used conventionally.

Binding Means and Latching Means of the Plate-Like Members

Said plate-like members are provided with a binding means and latching means of said plate-like members to maintain said hollow member, being the clipped object, in a clipped condition between said plate-like members, and as for the clip of the present embodiment, optional binding means or latching means used conventionally can be used. Especially by adapting latching means disclosed in the application on a clip as shown in FIG. 1, that the present inventor has filed previously (Patent Application No. 2001-127017), the object of the present invention can be attained more efficiently. As for the latching means of the previous application by the present inventor mentioned above, a latching means having a structure capable of releasing the latching of the latching part by using: a latching part; a supporting point part acting the latching releasing force added by the latching releasing means described hereinafter to the direction to release the latching of the latching part; the latching releasing means comprising at least the latching part, being bound to said latching means, transmitting the latching releasing force to said latching means, and having an effective function to release the latching of the latching part through the supporting point part, can be exemplified.

The present invention provides a clip that is able to form a separate space in a hollow member such as flexible tube or bag-like article and the like sufficiently in a liquid tight condition or to block its opening part, by said clipping hollow member, and that does not inhibit the fluid opening of the clipped part by said clipping.

The invention claimed is:

1. A clip to form independent spaces in a hollow member or to block an opening part of the hollow member, comprising:
    a first plate member having a groove formed in its entire longitudinal direction by two dentations joined to said first plate member by a root portion, wherein at least one of the dentations has a notch section formed in an outer surface of the root portion of the dentations, and the root portion of the dentations has a thinner wall as compared with portions other than the root portion; and
    a second plate member having a projection part formed in its entire longitudinal direction, wherein the projection part is highest in a central part of the second plate member in the longitudinal direction, and lowest at both end parts ends of the second plate member in the longitudinal direction.

2. The clip according to claim 1, further comprising dimples provided on at least one of the plate members in the longitudinal direction, wherein the dimples facilitate flow of fluid between the independent spaces of the hollow member after releasing the clip.

3. The clip according to claim 2, wherein the dimples are formed on opposing side surfaces of the central part of the at least one of the plate members.

4. The clip according to claim 1, wherein the root portion of the dentations is uniform in thickness.

5. The clip according to claim 1, wherein the hollow member is selected from the group consisting of a flexible tube and a bag.

* * * * *